(12) United States Patent
Grubbs et al.

(10) Patent No.: US 6,482,908 B1
(45) Date of Patent: Nov. 19, 2002

(54) TEMPLATE-DIRECTED RING-CLOSING METATHESIS AND RING-OPENING METATHESIS POLYMERIZATION OF FUNCTIONALIZED DIENES

(75) Inventors: Robert H. Grubbs, South Pasadena; Michael J. Marsella, Riverside; Heather D. Maynard, Sierra Madre, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/567,569

(22) Filed: May 5, 2000

Related U.S. Application Data

(62) Division of application No. 08/993,757, filed on Dec. 18, 1997, now Pat. No. 6,080,826.
(60) Provisional application No. 60/034,767, filed on Jan. 6, 1997, and provisional application No. 60/041,382, filed on Mar. 26, 1997.

(51) Int. Cl.[7] ........................... C08F 4/44; C07C 209/02
(52) U.S. Cl. ...................... 526/171; 526/172; 526/173; 558/381; 502/155; 502/167
(58) Field of Search ................................. 526/171, 172, 526/173; 558/381; 502/155, 167

(56) References Cited

U.S. PATENT DOCUMENTS 5,831,108 A * 11/1998 Grubbs et al. ................ 556/21

* cited by examiner

*Primary Examiner*—David W. Wu
*Assistant Examiner*—R. Harlan
(74) *Attorney, Agent, or Firm*—Pillsbury Winthrop LLP

(57) ABSTRACT

Functionalized cyclic olefins and methods for making the same are disclosed. Methods include template-directed ring-closing metathesis ("RCM") of functionalized acyclic dienes and template-directed depolymerization of functionalized polymers possessing regularly spaced sties of unsaturation. Although the template species may be any anion, cation, or dipolar compound, cationic species, especially alkali metals, are preferred. Functionalized polymers with regularly spaced sites of unsaturation and methods for making the same are also disclosed. One method for synthesizing these polymers is by ring-opening metathesis polymerization ("ROMP") of functionalized cyclic olefins. The metathesis catalysts for both RCM and ROMP reaction are ruthenium or osmium carbene complex catalysts of the formula
where M is Os or Ru; R and $R^1$ each may be hydrogen $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl; X and $X^1$ may be any anionic ligand; and L and $L^1$ may be any neutral electron donor.

34 Claims, No Drawings

TEMPLATE-DIRECTED RING-CLOSING METATHESIS AND RING-OPENING METATHESIS POLYMERIZATION OF FUNCTIONALIZED DIENES

The present application is a divisional of U.S. Application Ser. No. 08/993,757 filed Dec. 18, 1997 now U.S. Pat. No. 6,080,826 entitled TEMPLATE DIRECTED RING-CLOSING METATHESIS AND RING OPENING METATHESIS POLYMERIZATION OF FUNCTIONALIZED DIENES by inventors Robert H. Grubbs, Michael J. Marsella, and Heather D. Maynard.

This application claims the benefit of the following two U.S. Provisional applications both of which are incorporated herein by reference: (1) Application No. 60/034,767 filed Jan. 6, 1997 with title "Template Directed Ring Closing Metathesis and Ring Opening Metathesis Polymerization" and inventors Robert H. Grubbs, Michael Marsella, and Heather D. Maynard; and (2) Application No. 60/041,382 filed Mar. 26, 1997 with title "Template Directed Ring Closing Metathesis of Functionalized Dienes" and inventors Robert M. Grubbs, Michael J. Marsella, and Heather D. Maynard.

The U.S. Government has certain rights in this invention pursuant to Grant No. GM 31332-13 awarded by the National Institute of Health.

BACKGROUND

The present invention generally relates to the synthesis of functionalized cyclic olefins via template-directed ring-closing metathesis ("RCM") or template-directed depolymerization of functionalized unsaturated polymers, and to the synthesis of functionalized polymers by ring-opening metathesis polymerization ("ROMP"). More specifically, the present invention relates to specific crown-ether analogs possessing a site of unsaturation, and specific poly(ethylene glycol) analogs ("PEG analogs") possessing regularly spaced sites of unsaturation which may optionally include peptide fragments or other bioactive molecules.

Functionalized Cyclic Olefins

Functionalized cyclic molecules are an important class of compounds that are used extensively as metal-complexing species. These molecules have many uses including analytical chemistry titrations, removal of ions from solutions and soils, iron binding in hemoglobin, magnesium binding in chlorophyll, and for medicinal uses such as antimicrobial agents against gram-positive bacteria, fungi, viruses and the like. One particularly useful class of functionalized cyclic molecules are crown ethers which also find important uses as solubilizers for metals in organic transformation reactions. See *Crown Ethers and Analogs*, Patai, S. and Rappoport, Z. Eds; John Wiley & Sons: New York, 1989, which is incorporated herein by reference and contains many examples of technically and scientifically important functionalized cyclic molecules including crown-ethers, crown-thioethers, porphyrins, lariats, cryptands, sandwich complexes and the like.

When the functionalized cyclic molecules contain a site of unsaturation, as in the case of functionalized cyclic olefins, the site of unsaturation may be used for further chemical modification of the molecule. In addition, functionalized cyclic olefins may also be used as the starting materials for polymer synthesis via a ROMP reaction. As will be discussed in detail below, this is an important advantage since the ROMP of functionalized cyclic olefins provides a new method for synthesizing high molecular weight functionalized polymers which possess regularly spaced sites of unsaturation and regularly spaced functional groups. The sites of unsaturation of the polymer may be used for further chemical modification or may be used for covalent cross-linking of the polymer strands. In addition, the regularly spaced functional groups of the polymer may be used for further processing of the polymer. For example, the functional groups may be reacted together to cross-link the polymer strands, may be reacted with further components to modify the physical and chemical properties of the polymer, or if the polymer contains certain biologically active functional groups, may be used as biological receptor sites allowing the polymer to selectively adhere to different cell types.

Synthesizing functionalized cyclic olefins that possess a definite stereochemistry (i.e., cis or trans at the site of unsaturation) is also desirable since the differing conformation of the cis and trans isomers may give rise to different chelating properties for the functionalized cyclic olefins. In addition, the stereochemistry may also affect product yield. For example, in ROMP reactions of crown ether analogs, cis starting materials result in substantially higher polymer yields than the trans starting materials.

Recently, a novel class of metathesis catalysts based on ruthenium and osmium carbenes complex catalysts have been developed which are stable in the presence of a variety of functional groups. These catalysts are described in more detail below and their use has allowed for the synthesis of functionalized cyclic olefins.

Although the discovery of these catalysts has enabled the synthesis of functionalized cyclic olefins with five, six, seven, and eight membered rings, for all but these smallest sized rings, the conventional RCM approach typically results in low yields. In addition, entropic factors disfavor RCM reaction of larger sized rings and in many cases this gives rise to very small yields of ring-closed product when the ring size is greater than about seven. Moreover, large volumes of solvent are often required since the conventional reactions are usually run at high dilution to ensure the RCM reaction pathway is favored over the alternative reaction pathways of acyclic diene metathesis polymerization (ADMET) and ROMP of the cyclic olefin product.

In U.S. patent application Ser. No. 08/654,712 (which is incorporated herein by reference), a method developed by Grubbs, Miller, and Blackwell overcomes some of these drawbacks of the RCM reaction scheme for larger sized rings. In this method, acyclic diene starting materials are modified to possess a covalently-bonded conformational constraint. This constraint acts to favor the RCM reaction pathway over the other competing pathways and makes the RCM reaction more entropically favorable. Although successful at overcoming the problem of competing reactions and entropic factors, these covalent modification methods have serious drawbacks including the fact that the starting material must necessarily include a covalently-bonded conformational constraint. This restriction adds to the complexity of synthesizing the starting material and may severely restrict the acyclic dienes which may be used as RCM substrates. In addition to complicating the synthesis of the starting materials, the covalent conformational constraint must also be removed from the product cyclic olefin. The breaking of the covalently-bonded constraint may require extremely harsh reaction conditions which may cause further reactions of the functionalized olefin. In fact, in some cases this post processing of the cyclic olefins may be impossible to achieve or may at the very least, result in a much lower overall yield of cyclic product.

In summary, functionalized cyclic olefins are important for at least two reasons. First, the unsaturated molecules are analogs of saturated functionalized cyclic molecules such as crown-ethers and the site of unsaturation allows for further chemical modification of the molecule. Second, the unsaturated molecules may be used as the starting materials for a new method of synthesizing functionalized polymers possessing regularly spaced sites of unsaturation and regularly spaced functional groups. Functionalized cyclic olefins with small ring size (less than about seven) can be synthesized via the RCM of functionalized acyclic dienes; however, in many cases this method results in low yields when applied to larger sized rings due to the competing ROMP and ADMET pathways. In an effort to minimize the effect of the competing pathways the reaction can be run at high dilution. However, this leads to the use of large amounts of solvent. One method that is applicable to the synthesis of functionalized cyclic olefins with larger ring size includes the introduction of a covalent conformational constraint into the starting diene; however, this method has the important drawback that the covalent constraint must be removed from the cyclic olefin product. This post processing reaction may be costly, time consuming, and may damage the cyclic olefin product.

To overcome these drawbacks of the conventional methods, there therefore exists a need for a method for synthesizing functionalized cyclic olefins that is not limited to synthesizing only small ring size products, may not be required to be run at high dilution, and does not require starting materials that include covalent conformational constraints. In addition to these needs, it is also desirable that the method yield functionalized cyclic olefins with a definite stereo-chemistry at the olefin bond; preferably, a cis conformation.

Functionalized Unsaturated Polymers

Functionalized unsaturated polymers are also an important class of compounds. One illustrative example of polymers that may be synthesized using the methods of the present invention is PEG analogs, which may have important uses as a cell-selective biomaterial (i.e., as materials that can support selective adhesion of one cell type while resisting adhesion of other cell types). Selective adhesion of a biomaterial to one cell type has many important applications including the targeted delivery of drugs. One approach employed for obtaining cell-selective biomaterials is to synthesize a material resistant to all cell types and render the material adhesive to a certain cell type through the incorporation of cell adhesion substrates. In this design strategy, since only cells with specific receptors for the adhesion substrate may attach and spread, no other cells would be able to adhere to the surface. Because cell receptors can successfully bind to relatively small domains of adhesion proteins, short amino acid sequences can be employed as the adhesion substrates.

In one method used to synthesize cell-selective biomaterials, oligopeptides were grafted onto PEG immobilized, highly cross-linked polyacrylic acid networks (See Drumheller, P. D.; Hubbell, J. A. *Anal. Biochem.* 1994, 222, 380). In this approach, networks grafted with bioadhesive peptides supported complete cell adhesion, while those without peptides or with inactive control peptides remained nonadhesive to the cells. The PEG rendered the material nonadhesive to cells, and the acrylic acid provided points with which to graft the peptides.

In another approach, nonadhesive modified glass surfaces were rendered adhesive to cells through the immobilization of low concentrations of Arg-Gly-Asp (RGD) and Tyr-Ile-Gly-Ser-Arg (YIGSR) containing peptides. (See Massia, S. P.; Hubbell, J. A. *Anal. Biochem.* 1990, 187, 292). Cells spread at higher rates on the RGD surfaces than the YIGSR surfaces. Although it has been possible to synthesize specifically mediated cell adhesive materials using the conventional methods, these methods all suffer from the drawback that they cannot produce highly functionalized, highly derivatizable, well-controlled materials. In addition, most of the conventional methods involve chemically modifying a previously synthesized matrix, and using these methods it may be difficult to precisely control the chemical nature of the cell adhesive material.

To overcome the drawbacks of the conventional materials methods, there therefore exists a need for a method for synthesizing cell-selective, cell-adhesive materials that are highly functionalized, highly derivatizable, have well-controlled patterns of functionalization, and which use a direct synthesis of the cell-selective material from a peptide functionalized monomer starting material.

SUMMARY

The present invention addresses the above needs and provides a method for synthesizing functionalized cyclic olefins that is not limited to the synthesis of small ring sized products, needs not to be run at high dilution to overcome competing pathways, yields cyclic olefins of definite stereochemistry, and does not require the introduction of a covalent conformational constraint into the starting material. The present invention also provides specific crown ether analogs that may be useful both for applications listed in the Background section and as the starting materials for ROMP reactions to yield unsaturated functionalized polymers.

The invention also provides a method for synthesizing highly functionalized polymers possessing regularly spaced sites of unsaturation. One example of such polymers are cell-selective biomaterials that are highly functionalized, highly derivatizable, and have well-controlled patterns of functionalization. The invention also provides specific crown-ether and PEG analogs including crown-ether and PEG analogs that include peptide fragments. As described in the Background section, these materials are useful as cell-selective biomaterials.

The Catalyst

Ring-closing metathesis (RCM) and ring-opening polymerization (ROMP) reactions may be carried out by employing a ruthenium or osmium carbene complex catalyst that includes a ruthenium or osmium metal center in a +2 oxidation state, has an electron count of 16, and is penta-coordinated. The ruthenium or osmium carbene complex catalyst may have the formula where M is Os or Ru; R and $R^1$ each may be hydrogen, $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl; X and $X^1$ may be any anionic ligand; and L and $L^1$ may be any neutral electron donor. Specific limitations on the R, $R^1$, L, $L^1$, X, and $X^1$ groups are given in the detailed description section. In a preferred embodiment of the catalyst M is Ru; $R^1$ is hydrogen; R is selected from hydrogen; $C_1$–$C_{20}$ alkyl; aryl; $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and aryl substituted with one or more groups selected from the group consisting of $C_1$–$C_{20}$ alkyl, aryl, hydroxyl, $C_1$–$C_5$ alkoxy, amino, nitro, and halide; X and $X^1$ are Cl; and L and $L^1$ are selected from -$PPh_3$, -$P(cyclohexyl)_3$, -$P(cyclopentyl)_3$, and -$P(isopropyl)_3$.

The most preferred catalyst for use in the present invention is

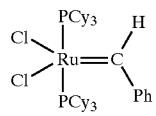

where Cy is cyclohexyl or cyclopentyl.

Functionalized Cyclic Olefins

The present invention provides novel functionalized cyclic olefins and methods for making the same. One method for synthesizing the functionalized cyclic olefins is by ring-closing metathesis. This method includes the steps of: (a) non-covalently conformationally restricting a functionalized acyclic diene; and (b) performing a ring-closing metathesis reaction on the conformationally restricted diene using the above described ruthenium or osmium carbene catalyst to yield a functionalized cyclic olefin.

Because the previously described ruthenium and osmium carbene catalysts are stable in the presence of a variety of functional groups, the acyclic diene starting material may contain one or more functional groups including but not limited to: hydroxyl, thiol, ketone, aldehyde, ester, ether, thioether, amine, amide, nitro acid, carboxylic acid, acid anhydride, disulfide, carbonate, carboalkoxy acid, isocyanate, carbodiimide, carboalkoxy, halogen, and quaternary amine. These functional groups may be incorporated in the backbone chain of the functionalized acyclic diene or may be incorporated in one or more pendant groups attached to the backbone chain of the functionalized acyclic diene.

In step (a) the non-covalent conformational restriction of the acyclic diene may be carried out by contacting the functionalized acyclic diene with a template species that includes an anionic species, a cationic species, or dipolar species. The preferred template species is a cationic species with alkali metal cations being the most preferred. The alkali metal cation may be derived from a dissociated alkali metal salt with the alkali metal perchlorate being the preferred salt. The most preferred template species is Li$^+$.

Another method for synthesizing functionalized cyclic olefins is by depolymerizing functionalized polymers possessing regularly spaced sites of unsaturation. This method includes the following steps: (a) non-covalently conformationally restricting a functionalized polymer possessing regularly spaced sites of unsaturation; and (b) performing a ring-closing metathesis reaction on the conformationally restricted polymer to yield a functionalized cyclic olefin.

In this embodiment, step (a) may be carried out in an analogous manner to the methods used for conformationally restricting the acyclic diene described in the first embodiment of the invention above; and step (b) may be carried out in an analogous manner to the methods used for ring-closing the acyclic diene described in the first embodiment of the invention above. For example, in a preferred embodiment of this aspect of the invention, a functionalized cyclic olefin may be synthesized by contacting a functionalized polymer possessing regularly spaced sites of unsaturation with the above described ruthenium or osmium carbene complex catalyst in the presence of a template species which may be selected from any one of anionic species, cationic species, and dipolar species.

Functionalized Unsaturated Polymer

Another embodiment of the invention provides functionalized unsaturated polymers possessing olefinic bonds regularly spaced along the backbone chain of the polymer and functional groups regularly spaced along the polymer chain. The functional groups may be either incorporated as part of the backbone polymer chain or may be incorporated as part of substituent pendant groups on the polymer chain. Illustrative functional groups include but are not limited to hydroxyl, thiol, ketone, aldehyde, ester, ether, thioether, amine, amide, nitro acid, carboxylic acid, acid anhydride, disulfide, carbonate, carboalkoxy acid, isocyanate, carbodiimide, carboalkoxy, halogen, and quaternary amine.

The functionalized unsaturated polymers of the present invention may also contain one or more amino acid residues, which may be incorporated in one or more pendant groups attached to the backbone chain of the functionalized unsaturated polymer. In preferred embodiments, the amino acid sequence includes -Arg-Gly-Asp- or -Gly-Gly-Arg-Gly-Asp-Ser-.

One method for synthesizing these functionalized polymers possessing regularly spaced sites of unsaturation includes the following steps: (a) synthesizing a functionalized cyclic olefin by the method described above; and (b) performing a ring-opening metathesis polymerization of the functionalized cyclic olefin to yield a functionalized unsaturated polymer.

Crown-Ether and PEG Analogs

Another embodiment of the invention provides a method for synthesizing crown-ether analogs possessing a site of unsaturation and includes the following steps: (a) forming a complex between a linear polyether diene of the formula

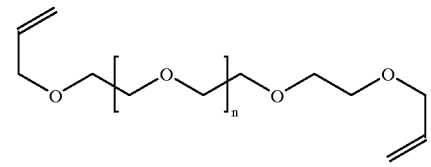

and an alkali metal cation (n is one or two); and (b) performing a ring-closing metathesis reaction of the complex to yield a crown-ether analog possessing a site of unsaturation. In this preferred embodiment, step (b) may be carried out in an analogous manner to the methods used for ring-closing the acyclic diene described in the first embodiment of the invention above.

Another embodiment of the invention provides a method for synthesizing poly(ethylene glycol) analogs possessing regularly spaced sites of unsaturation and includes the following steps: (a) synthesizing a crown-ether analog by the above method; and (b) performing a ring-opening metathesis polymerization of the crown-ether analog to yield a poly(ethylene glycol) analog possessing regularly spaced sites of unsaturation.

DETAILED DESCRIPTION

We have discovered that using certain ruthenium and osmium carbene complex catalysts together with a template species, it is possible to catalyze the RCM of functionalized acyclic dienes to yield unsaturated cyclic olefins. As will be described in detail below, this method allows for the synthesis of functionalized cyclic olefins without having to introduce covalently-bonded conformational constraints into the substrate diene. The method also yields functionalized cyclic olefins that possess a definite stereochemistry about the olefinic bond. By functionalized acyclic diene we mean a molecule that includes one or more functional groups and at least two olefinic bonds. The functionalized acyclic diene may include cyclic structures and may include more that two olefinic bonds; however, if the functionalized acyclic diene does contain cyclic structures at least two of the olefinic bonds must not be part of the cyclic structures.

The functional groups of the functionalized acyclic diene may be either incorporated as part of the backbone chain of the acyclic diene or may be incorporated in one or more substituent pendant groups on the backbone chain.

We have also discovered that the functionalized cyclic olefins synthesized by the above method may be used as substrates in a ROMP reaction to yield functionalized regularly unsaturated polymers. By functionalized regularly unsaturated polymers we mean polymers with olefinic bonds regularly spaced along the backbone chain of the polymer and functional groups regularly spaced along the polymer chain. The functional groups may be either incorporated as part of the backbone chain of the polymer or may be incorporated as part of substituent pendant groups on the polymer chain. In addition to the regularly space backbone olefinic bonds, the polymers may also contain olefinic bonds incorporated as substituent pendant groups on the polymer chain.

In addition to the above two applications, we have also discovered that using the ruthenium and osmium carbene complex catalysts together with a template species it is possible to catalyze the depolymerization of functionalized regularly unsaturated polymers to yield functionalized cyclic olefins. In this application, no matter what the stereochemistry of the unsaturated polymer about the olefinic bonds (eg. all cis, all trans, or mixed cis and trans), the functionalized cyclic olefin product of the depolymerization will possess a well-defined stereochemistry about the olefinic bond.

Last, initial studies indicate that a specific PEG analogs synthesized via the ROMP of a crown ether analog possess properties similar to PEG polymers. The PEG analogs may therefore be used in circumstances where PEG is useful. The PEG analog may also be modified to include amino acid residues and this modified PEG polymer may be selectively adhesive to cells, rendering it useful in tissue engineering and drug delivery applications.

We now describe these four aspects of the invention in greater detail. For clarity and ease of presentation, specific reaction conditions and procedures are collected together in the final Experimental Procedures section.

Catalysts That May be Used in the Present Invention

Generally, any metathesis catalyst that is stable in the presence of the functionalized substrate may be used in the present invention. Specifically, we have found that ruthenium or osmium carbene complex catalysts that include a ruthenium or osmium metal center that is in a +2 oxidation state, have an electron count of 16, and are pentacoordinated may be used in the present invention. More specifically, we have found that ruthenium or osmium carbene complex catalysts that include a ruthenium or osmium metal center bonded to a carbene ligand, two neutral electron donor ligands, and two anionic ligands are particularly suited for use in the present invention.

A specific embodiment of the catalyst has the formula where M is Os or Ru, and R, $R^1$, L, $L^1$, X and $X^1$ have the following meanings.

The R and $R^1$ substituents each may be the same or different and may be hydrogen or one of the following substituent groups: $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Each substituent group may optionally be substituted with one of the following groups: $C_1$–$C_5$ alkyl, halide, $C_1$–$C_5$ alkoxy, and phenyl; the phenyl may optionally be substituted with a halide, a $C_1$–$C_5$ alkyl, or a $C_1$–$C_5$ alkoxy. In a preferred embodiment, the R substituent is hydrogen and the $R^1$ substituent is selected from the following: hydrogen; $C_1$–$C_{20}$alkyl; aryl; $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and aryl substituted with one or more groups selected from the group consisting of $C_1$–$C_{20}$ alkyl, aryl, hydroxyl, $C_1$–$C_5$ alkoxy, amino, nitro, and halide. In a more preferred embodiment, the R substituent is hydrogen and the $R^1$ substituent is phenyl or phenyl substituted with a group selected from the group consisting of chloride, bromide, iodide, fluoride, —$NO_2$, —$NMe_2$, methoxy, and methyl. In the most preferred embodiment, the R substituent is hydrogen and the $R^1$ substituent is phenyl.

The L and $L^1$ ligands may be the same or different and may be any neutral electron donor ligand. In a preferred embodiment, the L and $L^1$ ligands may be the same or different and may be phosphines, sulfonated phosphines, phosphites, phosphinites, phosphonites, arsines, stibines, ethers, amines, amides, sulfoxides, carboxyls, nitrosyls, pyridines, and thioethers. In a more preferred embodiment, the L and $L^1$ ligands may be the same or different and are phosphines of the formula $PR^3R^4R^5$, where $R^3$ is a secondary alkyl or cycloalkyl group, and $R^4$ and $R^5$ are the same or different and may be aryl, $C_1$–$C_{10}$ primary alkyl, secondary alkyl, or cycloalkyl groups. In the most preferred embodiment, the L and $L^1$ ligands may be the same or different and are -P(cyclohexyl)$_3$, -P(cyclopentyl)$_3$, or -P(isopropyl)$_3$ ligands.

The X and $X^1$ ligands may be the same or different and may be any anionic ligand. In a preferred embodiment, the X and $X^1$ ligands may be the same or different and may be a halogen, or hydrogen or may be one of the following substituent groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Each substituent group may optionally be substituted with $C_1$–$C_5$ alkyl, halogen, $C_1$–$C_5$ alkoxy or with a phenyl group; the phenyl group may optionally be substituted with halogen, $C_1$–$C_5$ alkyl or $C_1$–$C_5$ alkoxy. In a more preferred embodiment, the X and $X^1$ ligands may be the same or different and may be Cl, Br, I, H, or may be one of the following functional groups: benzoate, $C_1$–$C_5$ carboxylate, $C_1$–$C_5$ alkyl, phenoxy, $C_1$–$C_5$ alkoxy, $C_1$–$C_5$ alkylthio, aryl, or $C_1$–$C_5$ alkyl sulfonate. Each functional group may optionally be substituted with $C_1$–$C_5$ alkyl or a phenyl group. The phenyl group may optionally be substituted with halogen, $C_1$–$C_5$ alkyl or $C_1$–$C_5$ alkoxy. In an even more preferred embodiment, the X and $X^1$ ligands may be the same or different and may be Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiment, X and $X^1$ are both Cl.

Preferred catalysts include the following:

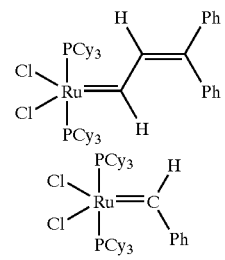

-continued

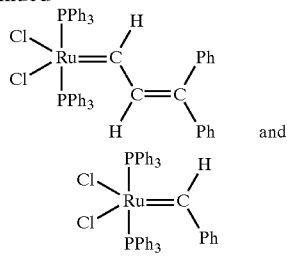

and

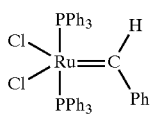

where Cy is cyclohexyl or cyclopentyl. The most preferred catalyst for use in the present invention has the formula

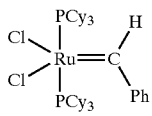

where Cy is cyclohexyl or cyclopentyl.

The catalysts that may be used in the present invention and methods of synthesizing these catalysts are presented in the following U.S. patents and U.S. patent applications, all of which are incorporated herein by reference: U.S. Pat. Nos. 5,312,940 and 5,342,909; U.S. patent applications Ser. No. 08/282,827, filed Jul. 29, 1994; 08/708,057, filed Aug. 30, 1996; 08/693,789, filed Jul. 31, 1996; and U.S. provisional application No. 60/031,088, filed Nov. 15, 1996.

These catalysts are stable in the presence of a variety of functional groups including hydroxyl, thiol, ketone, aldehyde, ester, ether, thioether, amine, imine, amide, nitro, carboxylic acid, acid anhydride, disulfide, carbonate, isocyanate, carbodiimide, carboalkoxy, halogen, and quaternary amine. The catalysts are also stable in the presence of naturally occurring and synthetic amino acids and peptides (see U.S. patent application Ser. No. 08/654,712) Therefore, the starting materials and products of the reactions described below may contain one or more of the above functional groups, amino acids or peptides without poisoning the catalyst. In addition, the catalysts are stable in the presence of aqueous, organic, or protic solvents, for example, aromatic hydrocarbons, chlorinated hydrocarbons, ethers, aliphatic hydrocarbons, alcohols, water, or mixtures of the above. Therefore, the reactions described below may be carried out in one or more of these solvents without poisoning the catalyst. Where appropriate, the reactions may also be carried out in the absence of a solvent. It is preferred to carry out the reactions in an aprotic, organic solvent for example methylene chloride or an ether.

Template-directed RCM of Functionalized Acyclic Dienes

This embodiment of the invention is directed to a method for synthesizing functionalized cyclic olefins by the template-directed RCM of a functionalized acyclic diene. By functionalized acyclic diene, we mean a molecule that contains one or more functional groups, amino acids, or peptides as described above and contains two or more olefinic bonds. The functionalized acyclic diene may contain one or more ring systems however at least two of the olefinic bonds must not both part of the same ring system. In this embodiment, a functionalized acyclic diene is contacted with a ruthenium or osmium carbene complex catalyst described above in the presence of a template species.

The template species may generally be any species that is capable of non-covalently bonding to the functionalized acyclic diene and thereby conformationally restricting the diene. Examples of template species include but are not limited to cations, anions, and dipolar molecules. Ionic species are the preferred template species with cationic species being most preferred. Examples of the type of non-covalent bonds that may be formed between the template and the diene include ionic interactions, dipolar interactions, ion/dipole interactions, ion/induced dipole interactions, higher multipolar interactions, dispersion force interactions, and hydrogen bonding interactions. Without being bound by theory, we hypothesize that the template species pre-organizes the diene into a conformation which facilitates the RCM step to form the cyclic olefin. The use of a template species becomes particularly important in the synthesis of cyclic olefins with large ring size. In this case, preorganization of the diene may be necessary for the RCM reaction to take place with appreciable yield since entropic factors will greatly disfavor the RCM reaction. Experimental results demonstrating this effect are presented below.

From a more microscopic point of view, this embodiment of the invention includes a two-step process: first, a functionalized acyclic diene is conformationally restricted via non-covalent interactions with a template species; and second, a RCM reaction of the unsaturated C—C bonds in the acyclic diene is catalyzed using the ruthenium or osmium carbene complex catalysts described above.

Since the ruthenium or osmium catalysts used in the RCM step are stable in the presence of a variety of functional groups, the functionalized acyclic diene starting material may contain one or more of the following functional groups: hydroxyl, thiol, ketone, aldehyde, ester, ether, thioether, amine, imine, amide, nitro, carboxylic acid, acid anhydride, disulfide, carbonate, isocyanate, carbodiimide, carboalkoxy, halogen, or quaternary amine groups. These functional groups may be either incorporated into the backbone carbon chain of the acyclic functionalized diene or may be substituted as pendant groups on the acyclic diene.

The functionalized acyclic diene starting materials may generally be synthesized using methods known in the art such as those described in the experimental section below or by olefination of an appropriate functionalized acyclic molecule. One skilled in the art would be capable of synthesizing the starting materials by olefinating functionalized acyclic molecules such as those described in Crown Ethers and Analogs. Preferred acyclic diene starting materials have been described in the summary section.

The RCM reaction may generally be carried out in any solvent that is substantially inert with respect to the metathesis catalyst and the starting and product molecules. Suitable solvents include aqueous, organic, or protic solvents, for example, aromatic hydrocarbons, chlorinated hydrocarbons, ethers, aliphatic hydrocarbons, alcohols, water, or mixtures of the above. Where appropriate, the RCM reaction may also be carried out in the absence of a solvent. It is preferred that the reactions be carried out in an aprotic organic solvent such as methylene chloride or an ether.

To demonstrate the concept of template-directed RCM using ruthenium and osmium carbene catalysts, we have carried out a series of experiments on the RCM of linear polyether dienes, the results of which are summarized below. While these experiments were carried out with polyether substrates, one of ordinary skill in the art, armed with the disclosure in this patent and their general knowledge of the field, would understand how to practice template-directed RCM for dienes which include the functional groups listed above.

Reaction Scheme 1 shows the synthesis of unsaturated cyclic polyethers 3 (n=1, 2) via the template-directed RCM of acyclic polyether diene 2 (n=1, 2). As depicted in Reaction Scheme 1 below, the synthesis of unsaturated cyclic polyether 3 via RCM of 2 is subject to two competing reaction pathways: (1) the ROMP of the RCM product 3 to yield polymer 4; and (2) ADMET of acyclic diene 2 to yield polymer 4. These alternative reaction pathways are discussed below, but in this section we investigate the RCM of polyether dienes 2 to yield the unsaturated crown-ether analogs 3.

To investigate the effect of the template species on the RCM reaction, the experiments were run at reaction conditions that are known to favor the RCM reaction over the completing ROMP and ADMET reactions. In this way it was possible to concentrate solely on the effect of the template species on the RCM reaction without the analysis of the experimental results being complicated by the effects of competing reactions.

closed product. For the 17-membered ring, 3 (n=2), the RCM reaction is enhanced by the addition of both $LiClO_4$ and $NaClO_4$ demonstrating that both $Li^+$ and $Na^+$ ions are capable of restricting the diene to a conformation favoring RCM. In addition to greatly increasing the product yield, it is evident from the results listed in Table 1 that the ions which function best as templates to give the highest yield of ring-closed product also favor the formation of the cis isomer. This trend implies that the cis isomer allows the macrocycle to adopt a conformation which best accommodates the template ion.

As depicted in Reaction Scheme 1, acyclic diene 2 may react via template-directed RCM to give ring-closed product 3 or via ADMET to give polymer 4. To investigate the ADMET reaction, we subjected acyclic diene 2 (n=1) to standard ADMET conditions (5 mole % 1, neat, 30 mtorr) at 50° C. which yielded relatively low molecular weight poly-

REACTION SCHEME 1

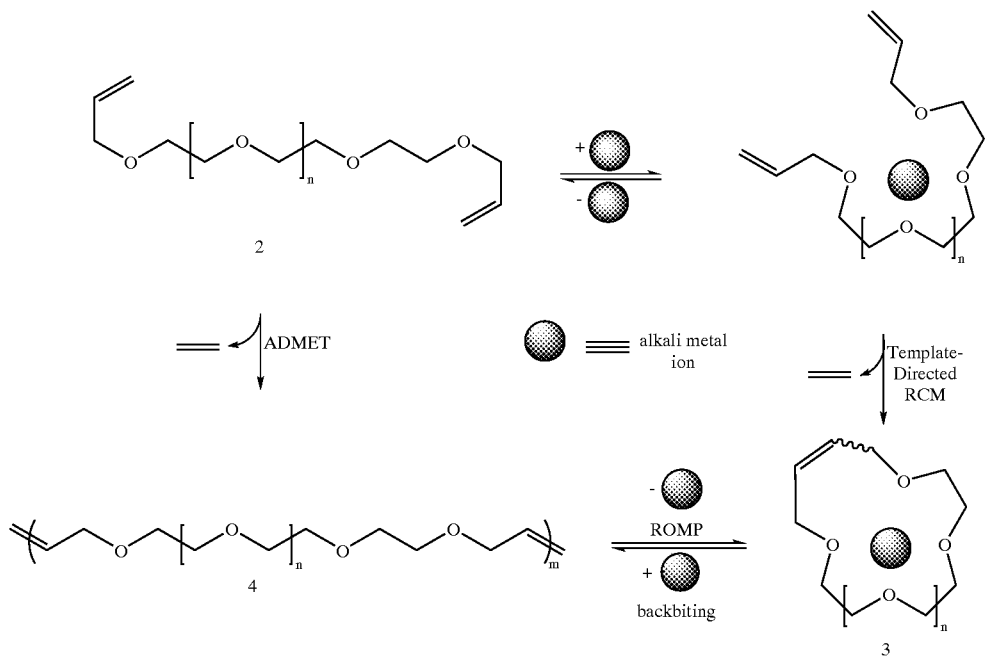

Specific reaction conditions for the RCM reactions are given in the Experimental Procedures section, and the results of these experiments are summarized in Table 1 below. All reactions were carried out using catalyst 1:

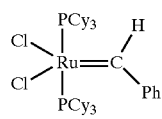

where Cy is cyclohexyl.

In these experiments the template species were $Li^+$, $Na^+$, and $K^+$ ions. Control experiments were also performed in the absence of template species. As can be seen from the results in Table 1, when the RCM reaction is conducted in the presence of a template species, the product yield is greatly enhanced compared to the yield of the non-template-directed reaction. For example, for the 14 member ring 3 (n=1), conducting the RCM reaction in the presence of a $Li^+$ template more than doubles the percent yield of the ringmer with $M_n$=11,200, PDI=3.4 (relative to polystyrene standards), and a cis:trans ratio of about 1:6.3. Isomerization of the allylic end groups of 2 to vinyl ethers was also observed as a minor byproduct, and this implies that the catalyst degradation to a ruthenium hydride may have occurred. The isomerization process is deleterious to further ADMET of the acyclic diene 2 as any remaining ruthenium carbene can react with the vinyl ether to yield a species inert to olefin metathesis.

As demonstrated by these experiments, the direct conversion of diene 2 to polymer 4 is not feasible by ADMET reaction; however, as depicted in Reaction Scheme 1, polymer 4 may be synthesized by the ROMP of cyclic olefin 3. This combination of template-directed RCM followed by ROMP offers a novel method for synthesizing functionalized regularly unsaturated polymers from functionalized acyclic diene starting materials.

Template-directed Depolymerization of Functionalized Unsaturated Polymers

Another aspect of the invention is the synthesis of functionalized cyclic olefins via template-directed depolymerization of functionalized polymers possessing regularly spaced sites of unsaturation. In this embodiment of the invention, a functionalized polymer possessing regularly spaced sites of unsaturation is contacted with a ruthenium or osmium carbene complex catalyst in the presence of a template species. The template species that may be used are the same as are described in the RCM section above and specific templates may be selected using the same criteria as described in that section. The functionalized cyclic olefins and functionalized polymers may contain one or more functional groups that may be either incorporated into the backbone chain of the cyclic olefin or polymer chain or may be substituted as pendant groups on the cyclic olefin or polymer chain.

To demonstrate the concept of template-directed depolymerization of unsaturated functionalized polymers using ruthenium and osmium carbene complex catalysts, we have carried out a series of experiments on the depolymerization of the poly(ethylene glycol) analogs.

One key feature of olefin metathesis is that, unlike other carbon-carbon bond forming reactions, the reversible formation and breaking of a carbon-carbon double bond allows the thermodynamic product distribution to be attained. This concept implies that unproductive coupling (i.e., "mistakes" which do not result in the desired product) can be "corrected" to yield the desired product if the template. effect is a significant driving force. It is also known that when dilute solutions of polymers obtained via ROMP are reacted with a metathesis catalyst, an equilibrium concentration of cyclic monomers is reestablished. In an attempt to exploit these processes, we explored the reaction between polymer 4 and catalyst 1 in the presence and absence of a template species; in this case, a Li$^+$ ion. It was anticipated that the template-directed "backbiting" of polymer 4 should yield macrocycle 3 (n=1). In the absence of a template, "backbiting" should result in a complex mixture of macrocycles of various ring sizes and linear oligomers. Performing the LiClO$_4$ templated degradation of polymer 4 under the conditions employed in the RCM conversion of acyclic diene 2 to cyclic olefin 3 resulted in a nearly quantitative conversion of polymer 4 to the cis isomer of cyclic olefin 3 (n=1). Polymer degradation in the absence of template gave about 20% combined yield of both cis and trans cyclic olefin 3 (n=1), and a mixture of low molecular weight oligomers (M$_n$≈9600). In addition to demonstrating the concept of template-directed backbiting, this result also illustrates the concept that if "mistakes" (i.e., ADMET dimers) are formed during template-directed RCM of 2, they can, in principle, be converted to 3 via this process.

Functionalized Cyclic Olefins

Another aspect of the invention pertains to functionalized cyclic olefin compounds themselves. The functionalized cyclic olefins described below may be synthesized using the inventive methods or any other applicable methods. One embodiment of this aspect of the invention provides functionalized cyclic olefins of the formula:

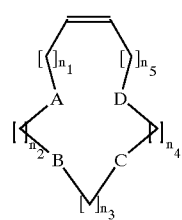

in which A, B, C, and D may be the same or different and may be —O—, —S—, ketone, amine, imine, amide, disulfide, carboalkoxy, an aromatic group, and a heterocyclic group; $n_1$, $n_2$, $n_3$, $n_4$, and $n_5$ may be the same or different and may be any non-negative integer. In a more preferred embodiment, A, B, C, and D are all —O— groups; $n_1$ and $n_5$ are equal to 1; and $n_2$, $n_3$, and $n_4$ are all equal to 2.

Another embodiment of the invention provides functionalized cyclic olefins of the formula

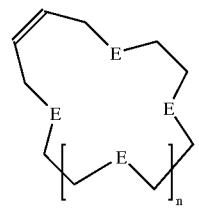

in which E is selected from —O—, —S—, ketone, amine, imine, amide, disulfide, carboalkoxy, an aromatic group, and a heterocyclic group; and n equals 1 or 2. In an even more preferred embodiment E is an ether group and n equals 1 or 2; that is, a functionalized cyclic olefin of the formula

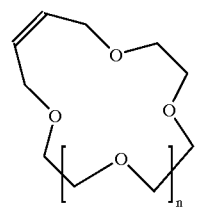

Another embodiment of the invention provides functionalized cyclic olefins of the formula

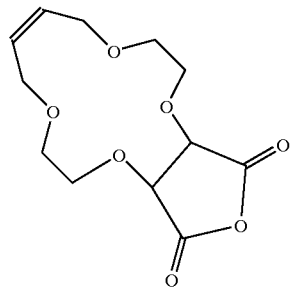

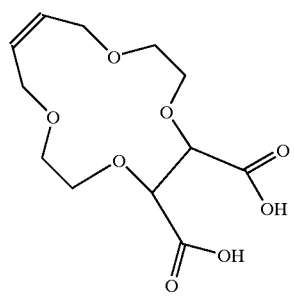

-continued

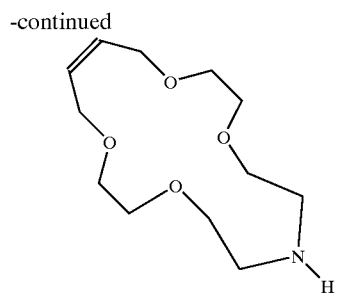

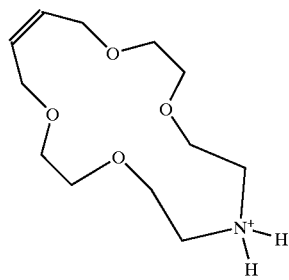

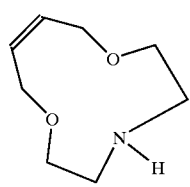

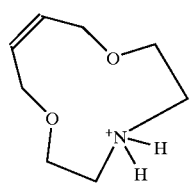

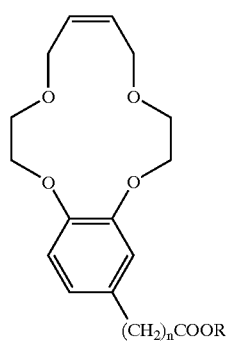

(CH$_2$)$_n$COOR wherein n is a non-negative integer and R is hydrogen, an aliphatic or an aromatic group.

The functionalized cyclic olefins of the present invention may also contain one or more amino acid residues, which may be incorporated in one or more pendant groups attached to the backbone chain of the functionalized acyclic diene. If the functionalized cyclic olefin is selected from one of the six given above, the amino acid residues may be attached via an amide bond to the carboxylate or amine groups. If the functionalized cyclic olefin includes amino acid residues, it is preferred that the functionalized acyclic diene is one of the following:

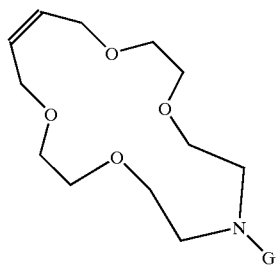

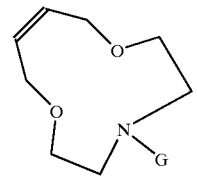

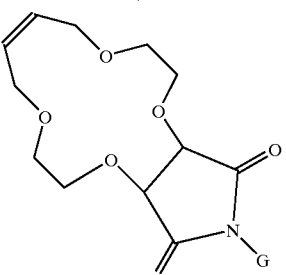

and

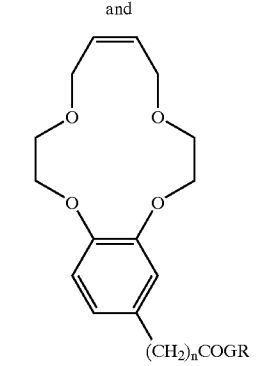

(CH$_2$)$_n$COGR wherein n and R are as previously defined and G contains one or more amino acid residues. In a preferred embodiment, G includes the amino acid sequence -Arg-Gly-Asp- (RGD); and in a more preferred embodiment G is -Gly-Gly-Arg-Gly-Asp-Ser- (GGRGDS) or -Phe-Gly-Arg-Gly-Asp-Ser- (FGRGDS).

ROMP of Functionalized Cyclic Olefins

Another aspect of the invention is the synthesis of functionalized polymers possessing regularly spaced sites of unsaturation via ROMP of functionalized cyclic olefins which have been synthesized by template-directed RCM. In this embodiment of the invention, a functionalized cyclic olefin synthesized via template-directed RCM is contacted with a ruthenium or osmium carbene complex catalyst described above to yield a functionalized regularly unsaturated polymer. The functionalized cyclic olefins and functionalized polymers may contain one or more functional groups that may be either incorporated into the backbone chain of the cyclic olefin or polymer chain or may be substituted as pendant groups on the cyclic olefin or polymer chain.

To demonstrate the concept of ROMP of functionalized cyclic olefins using ruthenium and osmium carbene catalysts, we have carried out a series of experiments on the ROMP of the unsaturated crown-ether analogs described in the preceding section and synthesized using template-directed RCM. The reaction conditions for carrying out the ROMP reactions (temperature, solvents, etc.) are well known in the art and are, for example, taught in U.S. patent application Ser. No. 08/282,827.

We examined the ROMP of 3 (n=1) initiated by catalyst 1 at various concentrations (1.2M, 10M, and neat) with a monomer to catalyst ("M/C") ratio of 100/1 and obtained polymers in >95% yield with $M_n$ values between 65,900 and 83,300 g/mol and PDIs between 1.7 and 1.96 (relative to polystyrene standards).

ROMP of 3 (n=1) was conducted utilizing various M/C ratios with all other conditions constant (1.2 M concentration, $CH_2Cl_2$, argon atmosphere, 4 hours). We obtained the results given in Table 2 below. As M/C is increased, the molecular weight of the resulting polymer increases; so by changing M/C, different molecular weights of 4 can be obtained. The yields decrease with increasing M/C because of the longer reaction times necessary to complete the polymerizations with high M/C (each polymerization was quenched after 4 hours for consistency). Increasing the reaction time should yield polymer with >95% conversion.

The polymerization of 3 (n=1) was conducted at 45° C. (100/1 M/C, 1.2 M, $CH_2Cl_2$, argon). The polymerization was complete (>95% yield) after 3 hours indicating that higher temperatures can be used to decrease the polymerization time of 3 (n=1). The polymer obtained from this reaction had a $M_n$=124,900 g/mol and PDI=2.0 (versus polystyrene standards).

Functionalized Unsaturated Polymer

Another aspect of the invention pertains to functionalized unsaturated polymers themselves. The functionalized unsaturated polymers described below may be synthesized using the methods described in this section or may be synthesized using other applicable methods.

Most generally, this embodiment of the invention provides functionalized unsaturated polymers possessing olefinic bonds regularly spaced along the backbone chain of the polymer and functional groups regularly spaced along the polymer chain. The functional groups may be either incorporated as part of the backbone polymer chain or may be incorporated as part of substituent pendant groups on the polymer chain and may include hydroxyl, thiol, ketone, aldehyde, ester, ether, thioether, amine, amide, nitro acid, carboxylic acid, acid anhydride, disulfide, carbonate, carboalkoxy acid, isocyanate, carbodiimide, carboalkoxy, halogen, and quaternary amine.

In a preferred embodiment, the functionalized unsaturated polymer includes one or more repeat units of the formula where A, B, C, and D may be the same or different and may be —O—, —S—, ketone, amine, imine, amide, disulfide, carboalkoxy, an aromatic group, and a heterocyclic group; $n_1$, $n_2$, $n_3$, $n_4$, and $n_5$ may be the same or different and may be any non-negative integer. In a more preferred embodiment, A, B, C, and D are all —O— groups; $n_1$ and $n_5$ are equal to 1; and $n_2$, $n_3$, and $n_4$ are all equal to 2.

In another preferred embodiment, the functionalized unsaturated polymer includes one or more repeat units of the formula
in which E is selected from —O—, —S—, ketone, amine, imine, amide, disulfide, carboalkoxy, an aromatic group, and a heterocyclic group; and n equals 1 or 2. In an even more preferred embodiment E is an ether group and n equals 1 or 2; that is, the polymer includes one or more repeat units of the formula Examples of preferred embodiments of the functionalized unsaturated polymers also include polymers containing one or more of the following repeat units
wherein n is a non-negative integer and R is hydrogen, an aliphatic or an aromatic group.

The functionalized unsaturated polymers of the present invention may also contain one or more amino acid residues, which may be incorporated in one or more pendant groups attached to the backbone chain of the functionalized unsaturated polymer. If the unsaturated polymer is selected from one of the six given above, the amino acid residues may be attached via an amide bond to the carboxylate or amine groups in the polymer. If the functionalized unsaturated polymer includes amino acid residues, it is preferred that the functionalized unsaturated polymer is one of the following:
wherein n and R are as previously defined and G contains one or more amino acid residues. In a preferred embodiment, G includes the amino acid sequence -Arg-Gly-Asp- (RGD); and in a more preferred embodiment G is -Gly-Gly-Arg-Gly-Asp-Ser- (GGRGDS) or -Phe-Gly-Arg-Gly-Asp-Ser- (FGRGDS).

Biomaterial Applications

Polymer 4 is analogous in structure to poly(ethylene glycol) [$(CH_2CH_2O)_n$], and is water soluble, and therefore has possible application in the field of biomaterials. For example, using template-directed ROMP it should be possible to synthesize highly functionalized analogs to PEG. These polymers may be selectively adhesive to cells, rendering them useful in tissue engineering applications. For reviews of tissue engineering see for example (a) Hubbell, J. A.; Langer, R. *C&EN* Mar. 13, 1995, 43; (b) Service, R. F., *Science*, 1995, 270, 1995; and (c) Hubbell, J. A. *Biotechnology* 1995, 13, 565. d) Peppas, N. A.; Langer, R. *Science*, 1994, 263, 1715.

One of the mechanisms by which a cell adheres to a material is through interaction of its cytoskeletally associated membrane receptors with absorbed adhesion proteins. An important class of cell receptors is the integrin family, and typical examples of adhesion proteins are fibronectin, vitronectin, and laminin. The first step in cell adhesion to a material is the absorption of proteins from biological fluids such as blood plasma onto the surface of the material. In most cases, protein absorption is energetically favorable because of the entropic gain associated with releasing the water from the relatively hydrophobic material surface. The cell receptors recognize and bind to small domains of the adhesion proteins, and the cells spread and flatten onto the surface of the material. In order to be non-adhesive to cells a material must be resistant to the initial adsorption of these cell adhesion proteins. Examples of such materials are quite rare, and polyethylene glycol (PEG) is an example of a biomaterial that has been studied for many years due to its resistance to protein absorption (See, for example, Harris, J. M., Ed.; *Poly(Ethylene Glycol) Chemistry Biotechnical and Biomedical Applications*; Plenum Press, New York, 1992, which is incorporated herein by reference).

Materials that can support selective adhesion of one cell type while resisting adhesion of other cell types have many potential applications (See, for example, Hubbell, J. A. *BioTechnology* 1995, 13, 565 and references therein). One approach to obtain a cell-selective biomaterial is to synthesize a material resistant to all cell types and render the material adhesive to a certain cell type through the incorporation of cell adhesion substrates. In this design strategy, only cells with specific receptors for the adhesion substrate may attach and spread; no other cells would be able to adhere to the surface.

Since it has been determined that cell receptors can successfully bind to relatively small domains of an adhesion protein, short amino acid sequences can be employed as the adhesion substrates. Several peptide sequences have been determined to bind integrin cell receptors, the most notable example is the Arg-Gly-Asp (RGD) sequence. For a review of RGD and cell adhesion see: Ruoslahti, E.; Pierschbacher, M. D. *Science*, 1987, 238, 491, which is incorporated herein by reference. For example, the oligopeptide Gly-Arg-Gly-Asp-Tyr (GRGDY) was immobilized onto a poorly adhesive glass substrate and found to be an extremely potent adhesion agent (Massia, S. P.; Hubbell, J. A. *J. Cell Biol.* 1991, 114, 1089). The results indicated that a minimum surface density of 10 fmol/cm$^2$ (~140 nm between peptides) was necessary to induce normal cell attachment and spreading. Therefore, immobilizing oligopeptides on a non-adhesive material surface can be an effective way to render the surface adhesive to a specific cell type.

Only a few materials have been fabricated that demonstrate specifically mediated cell spreading. In one example, oligopeptides were grafted onto PEG immobilized, highly cross-linked polyacrylic acid networks (Drumheller, P. D.; Hubbell, J. A. *Anal. Biochem.* 1994, 222, 380). Networks grafted with bioadhesive peptides supported complete cell adhesion, while those without peptides or with inactive control peptides remained nonadhesive to the cells. The PEG rendered the material nonadhesive to cells, and the acrylic acid provided points with which to graft the peptides. In another example, nonadhesive modified glass surfaces were rendered adhesive to cells through the immobilization of low concentrations of RGD and YIGSR containing peptides (Massia, S. P.; Hubbell, J. A. *Anal. Biochem.* 1990, 187, 292). Cells spread at higher rates on the RGD surfaces than the YIGSR surfaces.

None of the approaches to date in fabricating specifically mediated cell adhesive materials involve polymerizing a monomer that is covalently attached to an oligopeptide adhesion unit. The advantage of synthesizing a polymeric material by this method is the ability to produce a highly functional, highly derivatizable, well-controlled materials. Using the methods of the present invention it should be possible to synthesize directly a cell-selective polymer which can be derivitized with a variety of oligopeptide adhesion moieties as well as other functional ligands such as drugs. The following section describes work executed towards this end.

It is important that, for biomaterial applications, the PEG analogs of the present invention (e.g., polymer 4) be non-toxic to the body. In order to study the toxicity of polymer 4 synthesized as described above (100/1 monomer to catalyst ratio) the residual ruthenium metal must be removed. To this end different purification protocols were attempted. It was determined that precipitating the polymer slowly from methylene chloride into cold ether, followed by purification through a Chelex 100 bead column resulted in polymer that contained less than 0.01% ruthenium. The ruthenium concentration was determined using inductive-coupled plasma mass spectroscopy. Toxicity tests were conducted using this polymer sample, and the results are given in the next section.

The residual ruthenium concentration in a polymer can presumably be further reduced by decreasing the concentration of catalyst employed in the polymerization. To this end, ROMP of 3 was conducted utilizing various monomer to catalyst ratios (M/C) with all other conditions constant (1.2 M concentration in CH$_2$Cl$_2$, argon atmosphere, 4 hours). The results are given in Table 2, above. As expected, as the M/C increase, the molecular weights increase and the yields decrease. However, as stated previously the slightly lower yields may be rectified by increasing the reaction time. In summary, these results demonstrate that the original catalyst concentration can be reduced quite considerably.

One way to determine the cytotoxicity of a particular compound to a first approximation is to perform in vitro tests. To investigate the cytotoxicity of polymer 4, two tests where undertaken: a qualitative and a quantitative test.

In the first test, filter sterilized solutions of different concentrations of either 4 (containing 0.01% Ru) or PEG (20K) in a 150 µl of HEPES buffered saline solution (HBSS) were added to test wells. Human foreskin fibroblasts (HFFs) in cell culture medium (16 µl per well) were seeded into the wells at a density of 35,700 cells/cm$^2$. The final polymer concentrations in the wells were 0.01 wt %, 0.1 wt %, or 1 wt %. The cells were incubated for 24 hours and then were qualitatively observed under a phase contrast microscope. The cells were deemed alive if they were well-adhered to the bottom of the well, meaning they displayed flattened morphology with one or more cytoplasmic extensions. The cells were considered dead if they were rounded and/or floating in solution. As expected, the qualitative results for PEG evidenced that all cells were well-adhered. For polymer 4 the cells were well-adhered in 0.01 wt % and 0.1 wt % solutions of 4. However, all cells in 1.0 wt % of 4 were floating in solution and were dead.

In the second test, a quantitative approach was taken. First the HFFs were first seeded into polymer free test wells at a density of 35,700 cells/cm$^2$ and allowed to spread. After 24 hours, the medium was removed and new medium (16 µl per well) with sterilized solutions of 4 (two wells each of 0.01 wt %, 0.1 wt %, 1 wt %) in HBSS (150 µl per well) were added to the. wells. Two control wells with just HBSS were prepared along with PEG wells (one well of 20K PEG and one well of 100K PEG each containing 0.01 wt %, 0.1 wt %, 1 wt % polymer). The cells were incubated for 24 hours and then a live/dead test was performed.

In the live/dead test calcein AM was chosen as the live test because it is a substrate that is cleaved only in viable cells to produce a stain that fluoresces blue/green. Ethidium homodimer (EthD) was chosen as the dead test because it is a red fluorescent DNA stain that is able to pass through the compromised membranes of dead cells but not the membranes of live cells. The fluorescence emissions of the two probes are well resolved, so they can be used together in the same sample. Because the live and dead cells are stained different colors, fluorescein excitation optical filters (485 nm for Calcein AM and 530 nm for MD) were used to view the cells and quantitatively count the number of alive and dead cells.

The results of the test are given in Table 3. All PEG incubated wells contained >90% live cells, as is expected. The results for polymer 4 show that here too, >90% of cells incubated with 0.01 and 0.1 wt % of 4 were alive, but all cells incubated with 1 wt % 4 were dead. In this case polymer 4 contained 0.01% of residual ruthenium that was not able to be removed (see previous section); it is therefore difficult to determine if in the case of 1.0 wt % 4 it was the polymer or the ruthenium that was toxic to the cells. Given that some ruthenium complexes are known to be toxic, it is more likely the latter that was the cause of the death observed. As is demonstrated by the experimental results in Table 2, it is possible to reduce the original catalyst loading and using less catalysts we should be able to produce 1.0 wt % polymer solutions that are non-toxic to the cells.

In order to test the cell-adhesion properties of a polymer, it must be rendered water insoluble. This is usually accomplished by cross-linking the polymer. For example, PEG-diacrylate polymers have been synthesized and photopolymerized in the presence of an initiator to form hydrogels. Analogously, polymer 4-diacrylate was synthesized.

The synthesis of polymer 4-diacrylate was undertaken by employing a chain transfer agent (CTA). (Acylic olefins are known to act as chain transfer agents in the ROMP of cyclic olefins. See: Hillmyer, M. A.; Grubbs, R. H. *Macromolecules* 1995, 28, 8662, which is incorporated herein by reference) 1,4-bis(acetoxy)-cis-2-butene was employed in the polymerization of 3 (n=1) by ROMP (100/1 M/C, 20/1 M/CTA, $CH_2Cl_2$, argon atmosphere) as shown in Reaction Scheme 2. The resulting polymer with acetate end-groups had a number-average molecular weight of 18,600 g/mol and a PDI 2.04. The acetate groups were hydrolyzed with potassium carbonate to form the dialcohol. This polymer was treated with acryloyl chloride and triethylamine in refluxing THF to afford polymer 4-diacrylate. In each step the yield was quantitative.

As described in the previous sections, template-directed ring-closing metathesis of functionalized dienes (or their corresponding polymers) affords a high-yielding route into well-defined macrocycles which possess a site of unsaturation. Non-covalent interactions between the functionalized diene (or polymer) promote the ring-closing reactions, thus covalent structural modifications to the diene are not necessary. The protocol described here, using the appropriate template, affords a high yielding route into crown ethers, an important class of metal-complexing molecules. Specifically, a 12-crown-4 analog (3, n=1) was synthesized in high yield when $LiClO_4$ was employed as a template in the RCM of 2 (n=1). ROMP of 3 yields an unsaturated analog of PEG (4). This is the only route available to synthesize 4 as the ADMET of 2 results in low molecular polymer and oligomers. The subsequent template-directed depolymerization of 4 regenerates the 12-crown-4 analog (3, n=1).

The catalysts of the present invention are tolerant of a variety of functional groups, and so highly functionalized macrocycles (and thus polymers) should be readily obtainable by template-directed RCM. An illustrative example of a catechol monomer that was synthesized is compound 10 as shown by Reaction Scheme 3. Note that "F" represents the amino acid phenylalanine in Reaction Scheme 3. Other compounds of this type are also readily synthesized using variations of this method.

To incorporate oligopeptides into a PEG analog, it will be necessary to synthesize a monomer with attached oligopeptides and polymerize this monomer with ROMP. For example, monomer 13 as shown in Reaction Scheme 4 was synthesized. Note that -F-G-R-G-D-S- represents the peptide -Phe-Gly-Arg-Gly-Asp-Ser in Reaction Scheme 4. The ROMP of 13 should lead to a polymer with regular sites of functionality. Furthermore, monomer 13 may be copolymerized with 3 (n=1) to form a copolymer with functionality sites. Using the methods of the present invention, a skilled artisan will readily be able to extend this synthesis scheme to other functionalized monomers.

EXPERIMENTAL PROCEDURES

General. All reactions were performed using standard Schlenk techniques under an inert atmosphere of dry argon unless otherwise noted. $CH_2Cl_2$ and THF were purchased from Aldrich and purified using reported procedures. Tri- and tetraethylene glycol were dried over 4 Å sieves for 24 hours prior to use. Catalyst 1 was prepared according to literature procedures. All other reagents were purchased from Aldrich and used without further purification. NMR spectra were recorded on 300 MHz GE QE-300 spectrometers using $CHCl_3$ as internal reference. The molecular weights of polymers were determined using American Polymer Standards columns, an Altex solvent delivery system, and a Knauer Differential Refractometer at a flow rate of 1.0 ml/min in $CH_2Cl_2$. The molecular weights were reported relative to polystyrene standards purchased from PolySciences. Flash column chromatography was performed on 0.040–0.063 mm EM Separations silica gel purchased from VWR Scientific.

Compound 2 (n=1). To a stirred, room temperature solution of allyl bromide (58 mmol, 2 eq.) and NaH (64 mmol, 2.2 eq.) in THF (250 ml) was added dropwise triethylene glycol (29 mmol, 1 eq.) over a period of 1 hour. The reaction was allowed to stir at room temperature for a total of 24 hours. The mixture was extracted with $Et_2O/H_2O$, the organic layer was separated and dried over $Na_2SO_4$. The solvent was removed in vacuo, and the crude was chromatographed ($Et_2O$) to afford a colorless oil (53%–74% yield): $^1$H NMR (300 MHz, $CDCl_3$) δ 3.56 (m, 4H), 3.64 (br s, 8H), 3.99 (d, 4H), 5.18 (m, 4H), 5.88 (m, 2H); Anal. calcd for $C_{12}H_{22}O_4$: C, 62.56; H, 9.65; found: C, 60.60; H, 9.67.

Compound 2 (n=2). This compound was prepared exactly as described above for Compound 2 (n=1), substituting tetraethylene glycol for triethylene glycol. $^1$H NMR (300 MHz, $CDCl_3$) δ 3.56 (m, 4H), 3.64 (br s, 12H), 3.99 (d, 4H), 5.19 (m, 4), 5.90 (m, 2H); Anal. calcd for $C_{14}H_{26}O_5$: C, 61.28; H, 9.57; found: C, 60.42; H, 9.84.

Typical experimental procedure for template-directed ring-closing metathesis: synthesis of 3 (n=1) using $LiClO_4$ as template ion. Compound 2 (n=1) (100 mg, 0.434 mmol) and $LiClO_4$ (230 mg, 2.2 mmol) were dissolved in 2.0 ml THF and allowed to stir at room temperature until the $LiClO_4$ had dissolved. 20.0 ml of $CH_2Cl_2$ was added to the solution, and the mixture was stirred in a 50° C. oil bath. Catalyst 1 (18 mg, 0.022 mmol) was added to this solution via syringe. After stirring at 50° C. for 60 minutes, the reaction was exposed to air and approximately 0.05 ml of ethyl vinyl ether was added. The solvent was removed in vacuo, and the crude analyzed by $^1$H NMR to determine the yield and cis:trans ratio of 3 (n=1). Isolation of pure 3 (n=1) required three successive aqueous washings of $Et_2O$ solutions of 3 (n=1) to ensure complete removal of template salt. The $Et_2O$ solutions were dried over a minimal amount of $Na_2SO_4$, and then subjected to chromatography ($Et_2O$) to yield pure 3 (n=1). Because of the slight solubility of 3 in $H_2O$, isolated yields were lower than those determined by $^1$H NMR of the crude. $^1$H NMR (300 MHz, $CDCl_3$) δ 3.65–3.72 (m, 12H), 4.31 (d, 4H), 5.78 (t, 2H); $^{13}$C NMR (75 MHz, $CDCl_3$) 66.77, 68.72, 70.21, 71.77, 129.80; HRMS: calcd: 203.1284 (m+H$^+$), obsd. 203.1290 (m+H$^+$).

Typical Polymerization of compound 3 (n=1; cis). Catalyst 1 (0.00554 mmol, 1 eq.) was dissolved in $CD_2Cl_2$ (0.46 ml) and this solution was added to a reaction vessel containing 3 (n=1; cis) (0.554 mmol, 100 eq.). The reaction mixture was stirred vigorously at room temperature for 4 hours. The polymerization was terminated by addition of ethyl vinyl ether (ca. 0.1 ml) to the polymerization reaction. $^1$H NMR analysis of the crude reaction mixture showed a >95% conversion of 3 (n=1; cis) to polymer. The polymer was precipitated into cold $Et_2O$, centrifuged, isolated, and dried under vacuum to afford a 95% yield. Molecular weight determination (versus polystyrene standards): $M_n$=68,900 g/mol, $M_w$=117,400 g/mol, PDI=1.70; $^1$H NMR (500 MHz, $CDCl_3$) δ 3.58 (m, 6H), 3.64 (m, 6H), 4.01 (br d, 2H), 4.08 (br d, 2H), 5.71 (m, 1H), 5.80 (m, 1H); $^{13}$C NMR (100 MHz, CDCl$_3$) δ 66.90, 69.56, 70.69, 71.23, 129.60; Anal. calcd for C$_{10}$H$_{18}$O$_4$: C, 59.4, H, 8.97, found: C, 59.17; H, 9.33.

Typical experimental procedure for the depolymerization of polymer 4: LiClO$_4$ templated depolymerization. A CH$_2$Cl$_2$/THF solution (0.02M, CH$_2$Cl$_2$:THF 10:1) of polymer 4 (0.371 mmol, 1eq.), lithium perchlorate (1.860 mmol, 5eq.), and catalyst 1 (0.0186 mmol, 5 mol %) was stirred at 45° C. for 75 minutes. The reaction was terminated by addition of ca. 0.1 ml ethyl vinyl ether and then concentrated under vacuum. $^1$H NMR and GPC analysis of the crude showed a quantitative conversion of polymer 4 to macrocycle 3 (n=1; cis). The crude was dissolved in CH$_2$Cl$_2$ and washed several times with deionized water. The organic layer was concentrated under vacuum and purified by silica column chromatography (EtOAc) to afford 3 (n=1; cis) in an isolated yield of 83%. Analytical data for 3 (n=1; cis) were identical to those reported for its LiClO$_4$ templated RCM synthesis (see above).

Procedure for toxicity test #1. Polymers dissolved in HEPES buffered saline solution (HBSS) were filter (0.2 μm) sterilized and added to multiwell plates as described in the text. Human foreskin fibroblasts (HFF) of passage 5 were harvested using trypsin/EDTA (Sigma), washed with HBSS, resuspended in DMEM supplemented with 10% fetal bovine serum (FBS), 400 U/ml penicillin, and 400 mg/ml streptomycin (all from GIBCO), and seeded into 2 cm$^2$ wells. The wells were incubated for 24 hours at 37° C. and 5% CO$_2$ and after which time they were examined using phase contrast microscopy (Olympus CK 2, 100×). A cell was considered well adhered (alive) if it displayed flattened morphology and considered nonadhered (dead) if it displayed a rounded morphology or was floating in solution.

Procedure for toxicity test #2. HFF cells of passage 4 were harvested as above, and seeded into 2 cm$^2$ wells as described in the text, incubated for 24 hours at 37° C. and 5% CO$_2$, and then examined by phase contrast microscopy (Olympus CK 2, 100×). The medium was withdrawn and fresh supplemented DMEM and sterilized polymer HBSS solutions were added to the wells. The wells were incubated for another 24 hours at 37° C. and 5% CO$_2$ and were tested with the live/dead test described below.

Procedure for the live/dead test. A L/D solution containing 2 μM of calcein AM and 4 μm of ethidium homodimer (both from Molecular Probes) in HBSS was prepared right before use and kept in the dark. Wells from toxicity test #2 were aspirated, washed with HBSS, and aspirated again to assure complete removal of the medium and polymer. The L/D solution (100 μl) was added to each well, and the wells were incubated for 10 minutes at 37° C. and 5% CO$_2$ in the dark. The wells were viewed by fluorescence microscopy (Zeiss Microscope, 485 nm and 530 nm filters) and the number of live and dead cells were counted. A cell was deemed alive if it was colored green/blue with the 485 nm filter and deemed dead if the nucleus was stained red with the 530 nm filter. The percent live cells was determined by dividing the number of live cells with the total number of cells times 100. Each well was counted 3 times and the average was taken.

Synthesis of diacetate polymer (6) shown in Reaction Scheme 2. Catalyst 1 (5.9 mg, 0.00722 mmol) was dissolved in CH$_2$Cl$_2$ (0.60 ml) and this solution was added to a reaction vessel containing 3 (146 mg, 0.722 mmol.) and 1,4-bis(acetoxy)-cis-2-butene (6.2 mg, 0.0361 mmol) (5). The reaction mixture was stirred vigorously at 45° C. for 17 hours and terminated by the addition of ethyl vinyl ether (ca. 0.1 ml). The polymer was precipitated into cold ether, centrifuged, isolated, and dried under vacuum to afford a 100% yield of the polymer diacetate. Molecular weight determination (versus polystyrene standards): M$_n$=18 627 g/mol, M$_w$=38 079 g/mol, PDI=2.04. $^1$H NMR was the same as for polymer 4 with addition of the following resonances, indicating the end groups: (500 MHz, CDCl$_3$) δ 4.55 (m, 2H), 2.05 (s, 3H).

Synthesis of dialcohol polymer. To a solution of the above prepared diacetate polymer in methanol/water (3/1, 4 ml total) was added potassium carbonate (51 mg, 362 mmol, Aldrich). The reaction was stirred at room temperature for 12 hours, the pH was reduced to 7 with 10% citric acid and the reaction was stirred for an additional 2 hours. The solvent was removed in vacuo. and the residue taken up in CH$_2$Cl$_2$, and filtered. The solvent was evaporated and the product dried under hi-vacuum to afford 100% yield of the dialcohol substituted polymer. $^1$H NMR data for the dialcohol polymer were identical to those reported for 4.

Synthesis of diacrylate polymer. Acryoyl chloride (12 μl, 0.00014 mmol, Aldrich) was slowly added to a solution of the dialcohol polymer as prepared above and triethylamine (20 μl, 0.00014 mmol, Aldrich) in THF (1 ml). The mixture was refluxed for 5 hours, cooled, and filtered. The polymer was precipitated into hexanes, centrifuged, washed with hexanes (2 times), and dried under hi-vac to afford 100% of the diacrylate end capped polymer. $^1$H NMR was the same as for polymer 4 with addition of the following resonances, indicating the end groups: (500 MHz, CDCl$_3$) δ 6.37–6.43 (dd, 2H), 6.09–6.19 (in, 1H), 4.65 (in, 2H).

Synthesis of ethylene glycol allyl ether. To a 3-neck, round bottomed flask fitted with a reflux condenser and dropping funnel was added potassium hydroxide (16.8 g, 0.3 mmol, Aldrich) and ethylene glycol (16.7 ml, 0.3 mmol, Aldrich). The mixture was stirred under argon for 1 hour at 30–40° C. Allyl bromide (26.1 ml, 0.3 mmol, Aldrich) was added slowly over 2 hours. The reaction mixture was heated to 60° C. for 3 hours and cooled. The residue was extracted with ether, filtered, dried (MgSO$_4$), and the solvent removed in vacuo. The product was fractionally distilled (6–7.5 torr at 37–41° C. and column chromatographed twice (ether) to afford 12.9 g (42% yield) of 23 as a clear oil. $^1$H NMR (500 MHz, CDCl$_3$) δ 5.77–5.92 (m, 1H), 5.09–5.29 (m, 2H), 3.93–96 (m, 2H), 3.64–3.67 (t, 2H), 3.45–3.47 (t, 2H); $^{13}$C NMR (75 MHz, CDCl$_3$) δ 134.37, 117.33, 72.12, 71.47, 61.53; IR (NaCl plates) c,$^{-1}$: 3421.9, 3080.7, 3013.6, 2920.5, 2856.6, 1646.3, 1452.2, 1421.2, 1345.4, 1274.9, 1222.6, 1113.1, 1066.3, 995.8, 927.0, 887.5, 832.0; HRMS: calcd: 102.0636 (m+H+), obsd. 102.0638 (m+H+).

Synthesis of catechol derivatives. The following protocols may be generalized to any other catechol monomers.

Synthesis of 7

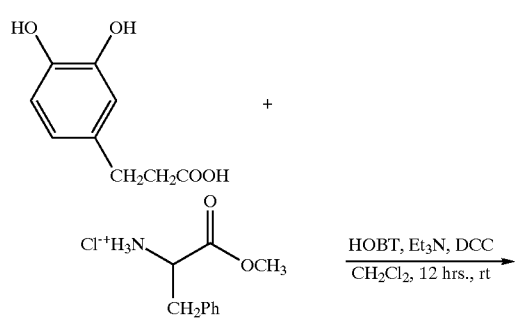

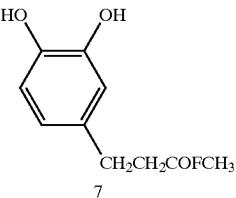

7

To a round bottom flask equipped with a stir bar was added phenylalanine methyl ester hydrochloride (1.328 g, 6.157 mmol), methylene chloride (0.2 M), and triethylamine (1.3 ml, 9.236 mmol). After stirring for 15 minutes, 3,4-dihydroxyhydrocinnamic acid (1.22 g, 6.157 mmol) and 1-hydroxybenzotriazole (1.082 g, 8.004 mmol) were added. The solution was stirred for 10 minutes and dicyclohexylcarbodiimide (1.270 g, 6.157 mmol) was added. The solution was stirred for 12 hours, filtered, and washed with 10% citric acid (1×), $H_2O$ (2×), and brine (1×). The organic layer was separated, dried over $MgSO_4$, and the solvent was removed in vacuo. The crude was purified by column chromatography (ethyl acetate) to afford 1.584 g (74.9% of 7 as a yellow solid. $^1$H NMR (300 MHz, $CDCl_3$) δ 2.49 (m, 2H), 2.83 (t, 2H), 3.07 (d, 2H), 3.74 (s, 3H), 4.91 (m, 1H), 6.15 (br d, 1H), 6.58 (dd, 1H), 6.75 (d, 1H), 6.83 (d, 1H), 6.98 (m, 2H), 7.29 (m, 2H). Note that "F" is the amino acid phenylalanine.

Synthesis of 9

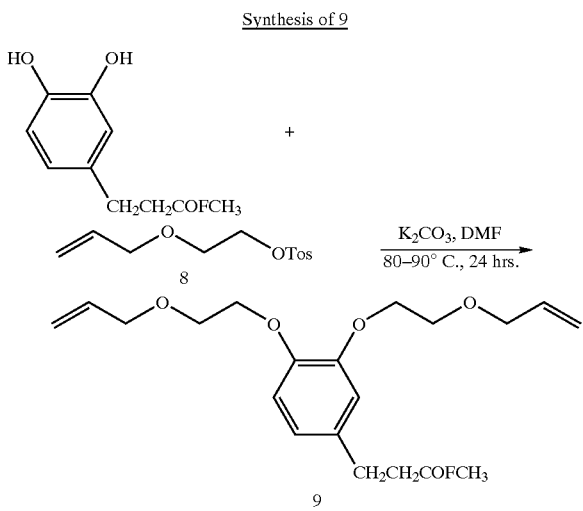

To a round bottom flask equipped with a stir bar was added 7 (341 mg, 0.992 mmol), 8 (508 mg, 1.984 mmol) anhydrous $K_2CO_3$ (548 mg, 3.968 mmol), and DMF (0.76 M). The solution was heated to 80–90° C. and stirred for 24 hours. Water was added and the aqueous layer washed with ether (3×). The ether fractions were collected and washed with $H_2O$ (3×), dried over $MgSO_4$, and the solvent was removed in vacuo. The crude was purified by column chromatography (7:3 ethyl acetate/hexanes) to afford 375 mg (74.0%) of 9 as a waxy white solid. $^1$H NMR (300 MHz, $CDCl_3$) δ 2.45 (m, 2H), 2.86 (m, 2H), 2.75 (d, 2H), 3.71 (s, 3H), 3.97 (q, 4H), 4.08 (m, 4H), 4.14 (m, 4H), 4.94 (m, 1H), 5.24 (m, 4H), 5.89 (m, 2H), 6.75 (m, 4H), 6.94 (m, 2H), 7.23 (m, 2H). Note that "F" is the amino acid phenylalanine.

Synthesis of 10 using $LiClO_4$ as a template

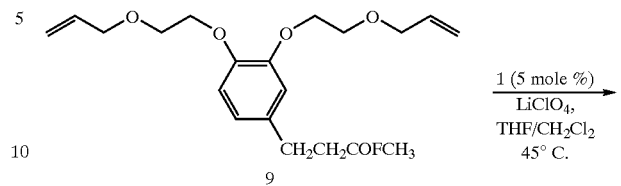

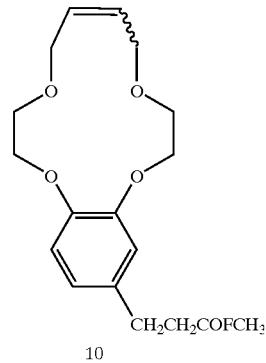

Compound 9 (177 mg, 0.346 mmol) and $LiClO_4$ (184 mg, 1.732 mmol) were dissolved in 1.6 ml of THF. 14.7 ml of $CH_2Cl_2$ was added to the solution and the mixture was heated to 45° C. Catalyst 1 (14.2 mg, 0.0173 mmol) in 1 ml of $CH_2Cl_2$ was added and the solution was stirred for 2 hours. The reaction mixture was cooled and approximately 0.5 ml of ethyl vinyl ether was added. The solvent was removed in vacuo, and the crude analyzed by $^1$H NMR to determine the yield and cis:trans ratio of 10. Isolation of pure 10 required dissolving the crude in $CH_2Cl_2$ and washing with $H_2O$ (1×). The solvent was removed in vacuo and the crude was further purified by column chromatography (ether followed by ethyl acetate. The crude was subjected to chromatography (50 ethyl acetate/hexanes) for a second time to yield 112 mg (67.0% yield, 6.2% trans) of 10 as an off-white solid. $^1$H NMR (300 MHz, $CD_2Cl_2$) δ 2.43 (m, 2H), 2.83 (t, 2H), 3.05 (dd, 2H), 3.69 (s, 3H), 3.81 (q, 4H), 4.11 (q, 4H), 4.35 (d, 4H), 4.83 (m, 1h), 5.72 (m, 2H), 5.88 (bd, 1H), 6.79 (m, 3H), 6.99 (m, 2H), 7.23 (m, 3H). Note that "F" is the amino acid phenylalanine.

Polymerization of 10

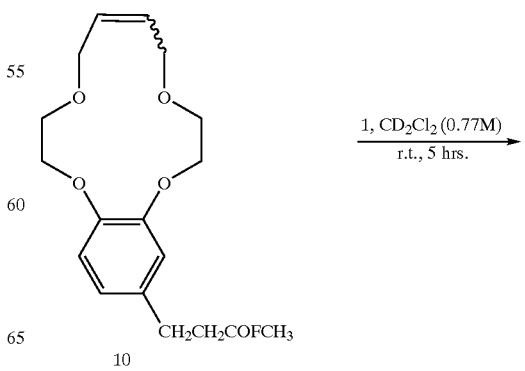

-continued

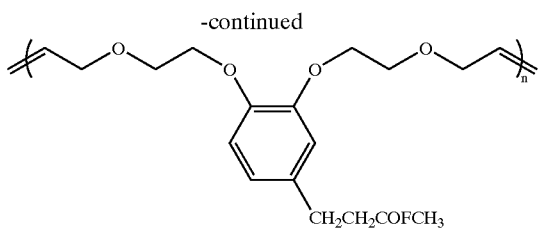

CH₂CH₂COFCH₃

Catalyst 1 (0.18 mg, 0.000213 mmol) in CD₂Cl₂ (27.8 μl) was added to a vial containing 10 (10.3 mg, 0.0213 mmol). The reaction mixture was stirred vigorously at room temperature for 5 hours. The polymerization mixture was diluted by approximately 1 ml of CD₂Cl₂ and 0.1 ml of ethyl vinyl ether was added. $^1$H NMR (300 MHz, CDCl₃) δ 2.45 (bm), 2.89 (bt), 3.67 (bd), 3.66 (bs), 3.76 (bt), 4.06 (bm), 4.80 (bm), 5.72 (bm), 5.82 (bm), 6.04 (bm), 6.75 (bm), 6.99 (bd), 7.24 (bm). This protocol may be generalized to other catechol polymers.

Synthesis of 11

Compound 10 (99 mg, 0.205 mmol) was dissolved in THF (0.5 ml). Then KOH (34 mg, 0.615 mmol) and H₂O (1.54 ml) were added and the solution was stirred for 24 hours. The solution was washed with CH₂Cl₂ and the aqueous layer was removed and acidified to a pH of 3. The aqueous layer was extracted with ether (5×). The ether layers were consolidated, dried over MgSO₄, filtered and the solution removed in vacuo. The crude was purified by column chromatography (3% acetic acid in ethyl acetate) to yield 69 mg (71.9%) of 11. $^1$H NMR (300 MHz, CD₃COCD₃) δ 2.47 (t, 2H), 2.74 (t, 2H), 2.95 (m, 1H), 3.19 (m, 1H), 3.75 (q, 4H), 4.08 (q, 4H), 4.33 (d, 4H), 5.64 (m, 2H), 6.68 (d, 1H), 6.83 (m, 2H), 7.19 (m, 5H).

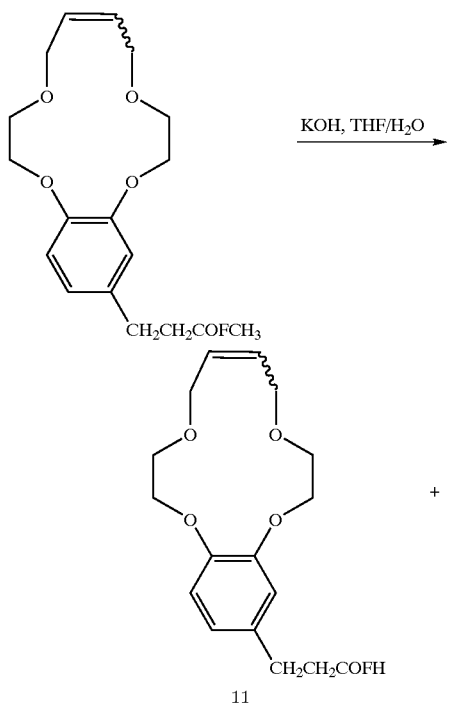

-continued

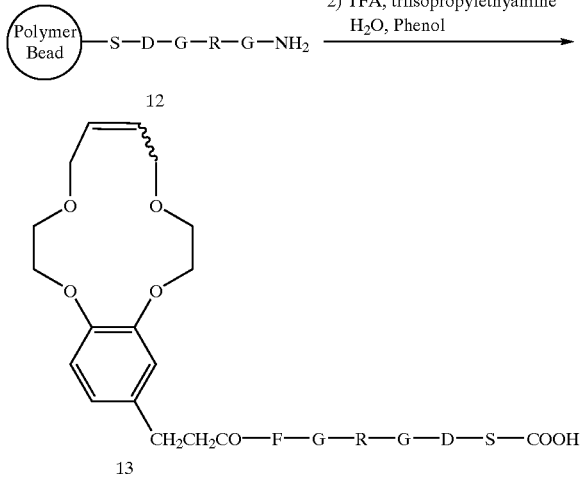

Resin 12 (248 mg, 0.123 mmol) was pre-swelled in DMF for 1 hr. The DMF was drained and 11 (69 mg, 0.147 mmol) and 1-hydroxybenzotriazole (19.9 mg, 0.147 mmol) in 1.2 ml of the coupling solution (consisting of an excess of 1,3-diisopropylcarbodiimide and a catalytic amount of N,N-diisopropylethylamine in DMF) was added and the mixture was agitated for 4.5 hrs. The solution was drained and the beads were rinsed with DMF (3×), CH₂Cl₂ (3×), and methanol (1×). The beads were dried under hi-vacuum overnight. Compound 13 was cleaved from the bead by adding a solution of TFA (8.8 ml), triisopropyl silane (0.2 ml), H₂O (0.5 ml), and phenol (0.5 ml) to the resin and reacting for 2 hours with shaking. Compound 13 was purified by filtering off the resin and precipitating into cold ether. The product was filtered and dried under vacuum to yield yellow, hydroscopic crystals of 13. The compound was assigned utilizing TOCSY NMR (500 MHz, D₂O), $^1$H NMR (300 MHz, D₂O) and electrospray.

What is claimed is:

1. A method for synthesizing a functionalized cyclic olefin by depolymerization of a functionalized polymer possessing regularly spaced sites of unsaturation, the method comprising the steps of
   (a) non-covalently conformationally restricting a functionalized polymer possessing regularly spaced sites of unsaturation; and
   (b) performing a ring-closing metathesis reaction of the conformationally restricted polymer to yield a functionalized cyclic olefin.

2. The method described in claim 1, wherein step (b) comprises contacting the conformationally restricted polymer with a ruthenium or osmium carbene complex catalyst that includes a ruthenium or osmium metal center that is in a +2 oxidation state, has an electron count of 16, and is pentacoordinated.

3. The method described in claim 1, wherein step (a) comprises contacting the functionalized polymer with a template species selected from the group consisting of anionic species, cationic species, and dipolar species.

4. The method described in claim 2 wherein the ruthenium or osmium carbene complex catalyst has the formula:
wherein:
M is selected from the group consisting of Os and Ru;

R and $R^1$ are the same or different and are selected from the group consisting of hydrogen, and a substituent group selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, and $C_1$–$C_{20}$ alkylsulfinyl;

X and $X^1$ are the same or different and are selected from any anionic ligand;

L and $L^1$ are the same or different and are selected from any neutral electron donor.

5. The method described in claim 4 wherein the substituent group is substituted with one or more groups selected from the group consisting of $C_1$–$C_5$ alkyl, halide, $C_1$–$C_5$ alkoxy, and phenyl.

6. The method described in claim 4 wherein L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

7. The method described in claim 6 wherein L and $L^1$ are each a phosphine of the formula $PR^3R^4R^5$ wherein $R^3$, $R^4$, and $R^5$ are each independently selected from the group consisting of aryl and $C_1$–$C_{10}$ alkyl.

8. The method described in claim 7 wherein L and $L^1$ are each independently selected from the group consisting of P(cyclohexyl)$_3$, P(cyclopentyl)$_3$, P(isopropyl)$_3$, and P(phenyl)$_3$.

9. The method described in claim 4 wherein X and $X^1$ are each independently selected from the group consisting of hydrogen, halogen, substituted moiety and unsubstituted moiety, wherein the moiety is selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl.

10. The method described in claim 4 wherein X and $X^1$ are each independently selected from the group consisting of halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate.

11. The method described in claim 10 wherein X and $X^1$ are both chloride.

12. The method described in claim 4 wherein:

M is Ru;

$R^1$ is hydrogen;

R is selected from the group consisting of
  (a) hydrogen;
  (b) $C_1$–$C_{20}$ alkyl;
  (c) aryl;
  (d) $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and
  (e) aryl substituted with one or more groups selected from the group consisting of $C_1$–$C_{20}$ alkyl, aryl, hydroxyl, $C_1$–$C_5$ alkoxy, amino, nitro, and halide;

X and $X^1$ are Cl; and

L and $L^1$ are the same or different and are selected from the group consisting of P(cyclohexyl)$_3$, P(cyclopentyl)$_3$, P(isopropyl)$_3$, and P(phenyl)$_3$.

13. The method described in claim 4, wherein the catalyst is selected from the group consisting of

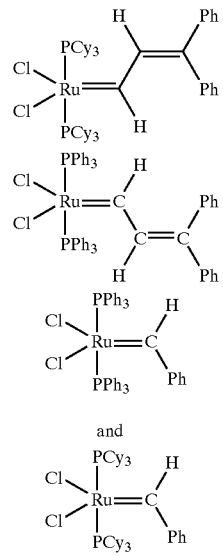

wherein Cy is cyclohexyl or cyclopentyl.

14. The method described in claim 3 wherein the template species is an alkali metal cation.

15. The method described in claim 14 wherein the alkali metal cation is derived from a disassociated alkali metal salt.

16. The method described in claim 15 wherein the alkali metal salt is an alkali metal perchlorate.

17. The method described in claim 14 wherein the template species is $Li^+$.

18. The method described in claim 17 wherein the $Li^+$ is derived from a disassociated Li salt.

19. The method described in claim 18 wherein the Li salt is $LiClO_4$.

20. The method described in claim 1 wherein the functionalized polymer contains one or more functional groups selected from the group consisting of hydroxyl, thiol, ketone, aldehyde, ester, ether, thioether, amine, amide, nitro acid, carboxylic acid, acid anhydride, disulfide, carbonate, carboalkoxy acid, isocyanate, carbodiimide, carboalkoxy, halogen, and quarternary amine.

21. The method described in claim 20 wherein the functional group is incorporated in the backbone chain of the functionalized polymer.

22. The method described in claim 20 wherein the functional group is incorporated in one or more pendent groups attached to the backbone chain of the functionalized polymer.

23. The method described in claim 1 wherein the functionalized polymer is a poly(ethylene glycol) analog.

24. The method described in claim 1 wherein the functionalized cyclic olefin contains one or more functional groups selected from the group consisting of hydroxyl, thiol, ketone, aldehyde, ester, ether, thioether, amine, amide, nitro acid, carboxylic acid, acid anhydride, disulfide, carbonate, carboalkoxy acid, isocyanate, carbodiimide, carboalkoxy, halogen, and quarternary amine.

25. The method described in claim 24 wherein the functional group is incorporated in the backbone chain of the functionalized cyclic olefin.

26. The method described in claim 24 wherein the functional group is incorporated in one or more pendent groups attached to the backbone chain of the functionalized cyclic olefin.

27. A method of synthesizing a cyclic olefin by depolymerization of a functionalized polymer possessing regularly spaced sites of unsaturation comprising contacting a functionalized polymer with a metathesis catalyst in the presence of a template species, wherein:

the metathesis catalyst is a ruthenium or osmium carbene complex catalyst that includes a ruthenium or osmium metal center that is in a +2 oxidation state, has an electron count of 16, and is pentacoordinated; and the template species is selected from the group consisting of anionic species, cationic species, and dipolar species.

28. The method described in claim 22, wherein the ruthenium or osmium carbene complex catalyst is selected from the group consisting of

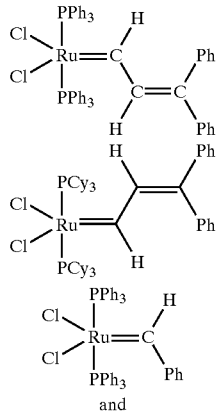

and

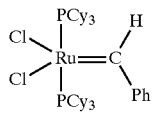

wherein Cy is cyclohexyl or cyclopentyl and the template is a $Li^+$ ion.

29. The method described in claim 27 wherein the template species is an alkali metal cation.

30. The method described in claim 29 wherein the alkali metal cation is derived from a disassociated alkali metal perchlorate.

31. The method described in claim 29 wherein the template species is $Li^+$.

32. The method described in claim 27 wherein the functionalized polymer contains one or more functional groups selected from the group consisting of hydroxyl, thiol, ketone, aldehyde, ester, ether, thioether, amine, amide, nitro acid, carboxylic acid, acid anhydride, disulfide, carbonate, carboalkoxy acid, isocyanate, carbodiimide, carboalkoxy, halogen, and quarternary amine.

33. The method described in claim 32 wherein the functional group is incorporated in the backbone chain of the functionalized polymer.

34. The method described in claim 33 wherein the functional group is incorporated in one or more pendent groups attached to the backbone chain of the functionalized polymer.

* * * * *